US006225292B1

(12) United States Patent
Raz et al.

(10) Patent No.: US 6,225,292 B1
(45) Date of Patent: May 1, 2001

(54) INHIBITORS OF DNA IMMUNOSTIMULATORY SEQUENCE ACTIVITY

(75) Inventors: Eyal Raz, Del Mar; Mark Roman, San Diego, both of CA (US)

(73) Assignees: The Regents of the University of California, Oakland; Dynavax Technologies Corp., Berkeley, both of CA (US)

(*) Notice: Subject to any disclaimer, the term of this patent is extended or adjusted under 35 U.S.C. 154(b) by 0 days.

(21) Appl. No.: 09/092,314

(22) Filed: Jun. 5, 1998

Related U.S. Application Data

(60) Provisional application No. 60/048,793, filed on Jun. 6, 1997.

(51) Int. Cl.[7] .................... A01N 43/04; A61K 38/00; C07H 21/02; C07H 21/04; C12Q 1/68
(52) U.S. Cl. .................... 514/44; 514/2; 536/23.1; 536/23.5; 435/6; 435/7.1; 435/91.1; 435/69.1; 435/366; 435/455; 436/513; 530/300
(58) Field of Search ................... 435/6, 7.24, 91.1, 435/91.5, 91.51, 366, 375, 455, 465; 514/44; 536/23.1, 23.4, 23.5, 24.3, 24.31, 24.32, 24.5, 25.3; 424/278.1

(56) References Cited

U.S. PATENT DOCUMENTS

| | | |
|---|---|---|
| 1,234,718 | 9/1917 | Hilleman et al. . |
| 3,725,545 | 4/1973 | Maes .................... 424/180 |
| 3,906,092 | 9/1975 | Hilleman et al. ............ 424/89 |
| 5,276,019 | 1/1994 | Cohen et al. ............... 514/44 |
| 5,278,302 | 1/1994 | Caruthers et al. ............ 536/24.5 |
| 5,286,365 | 2/1994 | Rudolph et al. ............. 514/44 |
| 5,331,090 * | 7/1994 | Lernhardt et al. ........... 530/329 |
| 5,453,496 | 9/1995 | Caruthers et al. ............ 536/24.5 |
| 5,703,055 | 12/1997 | Felgner et al. .............. 514/44 |
| 5,968,909 * | 10/1999 | Agrawal et al. .............. 514/44 |

FOREIGN PATENT DOCUMENTS

| | | |
|---|---|---|
| 0173254 * | 8/1985 | (EP) . |
| 0330227 * | 2/1989 | (EP) . |
| 0 468 520 A2 | 1/1992 | (EP) . |
| 9103251 * | 3/1991 | (WO) . |
| PCT/US95/03547 | 6/1995 | (WO) . |
| WO 95/26204 | 10/1995 | (WO) . |

(List continued on next page.)

OTHER PUBLICATIONS

Branch,A 1998 Trends in Bioch. Sci. (TIBS) vol. 23, pp. 45–50.*

(List continued on next page.)

Primary Examiner—Remy Yucel
Assistant Examiner—Jane Zara
(74) Attorney, Agent, or Firm—Paula A. Borden; Bozicevic, Field & Francis LLP

(57) ABSTRACT

The invention consists of oligonucleotides which inhibit the immunostimulatory activity of ISS-ODN (immunostimulatory sequence oligodeoxynucleotides) as well as methods for their identification and use. The oligonucleotides of the invention are useful in controlling therapeutically intended ISS-ODN adjuvant activity as well as undesired ISS-ODN activity exerted by recombinant expression vectors, such as those used for gene therapy and gene immunization. The oligonucleotides of the invention also have anti-inflammatory activity useful in reducing inflammation in response to infection of a host with ISS-ODN containing microbes, in controlling autoimmune disease and in boosting host Th2 type immune responses to an antigen. The invention also encompasses pharmaceutically useful conjugates of the oligonucleotides of the invention (including conjugate partners such as antigens and antibodies).

82 Claims, 5 Drawing Sheets

FOREIGN PATENT DOCUMENTS

| | | |
|---|---|---|
| WO | | |
| 96/02555A1 | 2/1996 | (WO) . |
| WO96/02555 | 2/1996 | (WO) . |
| 9810066 * | 3/1998 | (WO) . |
| WO 98/18810 | 5/1998 | (WO) . |
| WO98/18810 | 5/1998 | (WO) . |
| WO98/37919 | 9/1998 | (WO) . |
| WO98/40100 | 9/1998 | (WO) . |
| WO98/52581 | 11/1998 | (WO) . |
| 9853075 * | 11/1998 | (WO) . |

OTHER PUBLICATIONS

Crooke, St. 1998 Antisense Research & Applications., Chapter 1, pp 1–50. Publisher—Springer.*

Delphine J. Lee et al., "Inhibition of IgE Antibody Formation by Plasmid DNA Immunization Is Mediated by Both CD4+ and CD8+ T Cells", 1996, Int'l Archives of Allergy and Immuunology 113/1–3/97.

Yamamoto, "Mode of Action of Oligonucleotide Fraction Extracted From Mycobacterium Bovis BCG", National Institute of Health, 1994 Tokyo Japan.

"Biochemical and Biophysical Research Communications", Sep. 30, 1993, Academic Press, Inc.

Sato, et al., "Immunostimulatory DNA Sequences Necessary for Effective Intradermal Gene Immunization", 1996, Science vol. 273.

Warren, "Adjuvants", 1992, XP–002058362.

Eyal Raz, et al., "Cytokines and Inflammatory Mediators" Oct. 20, 1996, XP–002058356.

Corry, et al., "Interleukin 4, but Not Interleukin 5 or Eosinophils, Is Required in a Murine Model of Acute Airway Hyperreactivity," 1996, The Rockefeller University Press, vol. 183 Jan. 1996.

"Bacterial DNA Causes Septic Shock", Nature, vol. 386, Mar. 27, 1997.

Nakagawa, et al., "Immunotherapy of Allergic Diseases", Int Arch Allergy Immunol 1993.

Manickan, et al. "Enhancement of Immune Response to naked DNA Vaccine by Immunization with Transfected Dendritic Cells", 1997, Journal of Leukocyte Biology, vol. 61.

Meeting Report, "International Meeting on the Nucleic Acid Vaccines for the Prevention of Infectious Disease and Regulating Nucleic Acid (DNA) Vaccines", 1996, Natcher Conference Center NIH.

Pardoll, et al. "Exposing the Immunology of Naked DNA Vaccines" Baltimore, Maryland 21205.

Hohlfeld, et al. "The Immunobiology of Muscle" Immunology Today, vol. 15 1994.

Ballas, et al. "Induction of NK Activity in Murine and Human Cells by CpG Motifs in Oligodeoxynucleotides and Bacterial DNA[1]" XP–002058359, The American Association of Immunologists, 1996.

Branda, et al. "Amplification of antibody production by phosphorothioate oligodeoxynucleotides" XP–002058361, 1996 by Mosby–Year Book, Inc.

Raz, et al. Preferential induction of a Th1 immune response and inhibition of specific IgE antibody formation by plasmid DNA immunization Proceedings of the National Academy of Sciences of the United States of America May 14, 1996, vol. 93/No. 10.

Fuller, et al. "A Qualitative Progression in HIV Type 1 Glycoprotein 120–Specific Cytotoxic Cellular and Humoral Immune Responses in Mice Receiving a DNA–Based Glycoprotein 120 Vaccine," AIDS Research and Human Retroviruses, vol. 10, Nov. 1994.

Feltquate, et al. "Different T Helper Cell Types and Antibody Isotypes Generated by Saline and Gene Gun DNA Immunization", The Journal of Immunology, 1997 The American Association of Immunologists.

Lee, et al. Inhibition of IgE Antibody Formation by Plasmid DNA Immunization Is Mediated by both CD4+ and CD8+ T Cells, 1996, Salzburg, Austria.

Raz, et al. "Intradermal gene immunization: The possible role of DNA uptake in the induction of cellular immunity to viruses" Medical Sciences, Sep. 1994.

Mader, et al. "A steroid–inducible promoter for the controlled overexpression of cloned genes in eukaryotic cells," Biochemistry, Bol. 90, pp 5603–5607, Jun. 1993.

Kemeny, et al. "CD8+ T cells in allergy," Basic Review Article, 1992.

Secrist, et al. "Allergen Immunotherapy Decreases Interleukin 4 Production in CD4+ T Cells from Allergic Individuals," The Rockefeller University Press, Dec. 1993.

Multi–Test Directions for Use, New York 11050 1988.

Terr, "Allergy Desensitization," Chapter 56, pp. 739–743 1992.

Nakagawa, et al. "Immunotherapy of Allergic Diseases," Int Arch Allergy Immunol, 1993.

Davis, et al. "Plasmid DNA Is Superior to Viral Vectors for Direct Gene Transfer into Adult Mouse Skeletal Muscle," Human Gene Therapy, 4:733–740.

Ramsay, et al. "Enhancement of Mucosal IgA Responses by Interleukins 5 and 6 Encoded in Recombinant Vaccine Vectors," Reproduction, Fertility and Development, Australia, 1994.

Mojcik, et al. "Administration of a Phosphorothioate Oligonucleotide Antisense to Murine Endogenous Retroviral MCF env Causes Immune Effects in Vivo in a Sequence–Specific Manner," Clinical Immunology and Immunopathology, vol. 67, 1993.

Messina, et al. "The Influence of DNA Structure in the In Vitro Stimulation of Murine Lymphocytes by Natural and Synthetic Polynucleotide Antigens[1]," Cellular Immunology, vol. 147, Mar. 1993.

Messina, et al. "Stimulation of In Vitro Murine Lymphocyte Proliferation by Bacterial DNA[1]," The Journal of Immunology, 75th Anniversary, vol. 147, Sep. 1991.

Yamamoto, et al. "Unique Palindromic Sequences in Synthetic Ologonucleotides are Required to Induce INF and Augment INF–Mediated Natural Killer Activity[1]," The Journal of Immunology, vol. 148, Jun. 1992.

Tanaka, et al. "An Antisense Oligonucleotide Complementary to a Sequence in Iγ2b Increases γ2b Germline Transcripts, Stimulated B Cell DNA Synthesis, and Inhibits Immunoglobulin Secretion," The Journal of Experimental Medicine, The Rockefeller University Press, vol. 175, 1992.

Krieg, "CpG DNA: A Pathogenic Factor in Systemic Lupus Erythematosus?" Journal of Clinical Immunology, Plenum Press, New York and London, vol. 15, Jan. 1995.

Jachimczak, et al. "The effect of transforming growth factor $-\beta_2$–specific phosphorothioate–anti–sense oligodeoxynucleotides in reversing cellular immunosuppression in malignant glioma," Journal of Neurosurgery, Apr. 1993, vol. 78.

Krieg, et al. "CpG Motifs in bacterial DNA trigger direct B–cell activation," Nature International Weekly Journal of Science, vol. 374, No. 6522, Apr. 1995.

Jyonouchi, et al. "Immunomodulating Actions of Nucleotides: Enhancement of Immunoglobulin Production by Human Cord Blood Lymphocytes," Pediatric Research, vol. 64, Aug. 1993.

Pisetsky, et al. "Stimulation of Murine Lymphocyte Proliferation by a Phosphorothioate Oligonucleotide with Antisense Activity for Herpes Simplex Virus," Life Sciences, 1993.

Iguchi–Ariga, et al. "CpG methylation of the cAMP–responsive enhancer/promote sequence TGACGTCA abolishes specific factor binding as well as transcriptinal activation," Genes & Development, 1989.

Krieg, et al. "A Role for Endogenous Retroviral Sequences in the Regulation of Lymphocyte Activation," The Journal of Immunology, vol. 143, 1989.

Ewel, et al. "Polyinosinic–Polycytidylic Acid Comlexed with Poly–L–lysine and Carboxymethylcellulose in Combination with Interleukin 2 in Patients with Cancer: Clinical and Immunological Effects[1]," Cancer Research, Jun. 1992.

Sano, et al. "Binding Properties of Human Anti–DNA Antibodies to Cloned Human DNA Fragments," Immunology, 1989.

Nishida, et al. "Definition of a GC–rich motif as regulatory sequence of the human IL–3 gene: coordinate regulation of the IL–3 gene by CLE2/GC box of the GM–CSF gene in T cell activation," International Immunology, vol. 3, 1991.

Bennett, et al. "DNA Binding to Human Leukocytes," The American Society for Clinical Investigation, Inc., Dec. 1985.

Robinson, et al. "Use of direct DNA inoculations to elicit protective immune responses," Journal of Cellular Biochemistry, Mar. 1993.

Ulmer, et al. "Heterologous Protection Against Influenza by Injection of DNA Encoding a Viral Protein," Science, vol. 259, Mar. 1993.

Kimura, et al. "Binding of Oligoguanylate to Scavenger Receptors Is Required for Ologonucleotides to Augment NK Cell Activity and Induce IFN," J. Biochem, vol. 116, 1994.

Yamamoto, et al. "Ability of Oligonucleotides with Certain Palindromes to Induce Interferon Zproduction and Augment Natural Killer Cell Activity Is Associated with Their Base Length," Antisense Research and Development, 1994.

Yamamoto, "Lipofection of Synthetic Ologodeoxyribonucleotide Having a Palindromic Sequence of AACGTT to Murine Splenocytes Enhances Interferon Production and Natural Killer Activity," Microbiol. Immunol. 38(10), 1994.

Yakubov, et al. "Mechanism of oligonucleotide uptake by cells: Involvement of specific receptors?" Proc. Natl. Acad. Sci. USA, Sep. 1989.

Schleimer, et al. "IL–4 Induces Adherence of Human Eosinophils and Basophils but not Neutrophils to Endothelium," The Journal of Immunology, 1992.

Zhao, et al. "Comparison of Cellular Binding and Uptake of Antisense Phosphodiester, Phosphorothioate, and Mixed Phosphorothioate and Methylphosphonate Oligonucleotides," Antisense Research and Development, vol. 3, Spring 1993.

Tam, et al. "Ologonucleotide–Mediated Inhibition of CD28 Expression Induces Human T Cell Hyporesponsiveness and Manifests Impaired Contact Hypersensitivity in Mice," The Journal of Immunology, vol. 158, Jan. 1997.

Hawkins, et al. Editorial, "Toward Genetically Targeted Research and Therapeutics," Antisense Research and Development, 1992.

Sedegah, et al., "Protection against malaria by immunization with plasmid DNA encoding circumsporozoite protein," Proc. Nutl. Acad. Sci. USA, vol. 91, pp. 9866–9870, Oct. 1994, Immunology.

D. Xu, et al., "Protection against leishmaniasis by injection of DNA encoding a major surface glycoprotein, gp63, of L. Major," Immunology, 173–176; Nov. 1994.

Pisetsky, et al., Immunology Properties of Bacterial $DNA^{\alpha}$, Annals New York Academy of Sciences, pp. 152–163.

Klinman, et al., Contribution of CpG Motifs to the Immunogenicity of DNA Vaccines[1], The American Association of Immunologists, vol. 158, No. 8, Apr. 1997.

Krieg, Arthur M., Lymphocyte activation by CpG dinucleotide motifs in prokaryotic DNA, Trends in Microbiology, vol. 4, No. 2, Feb. 1996.

Tripathy, et al., "Immune responses to transgene–encoded proteins limit the stability of gene expression after injection of replication–defective adenovirus vectors," May 1996, Nature Medicine, vol. 2 No. 5.

Conboy, et al., "Novel genetic regulation of T helper 1 (Th1)/Th2 cytokine productionand encephalitogenicity in inbred mouse strains." Feb. 3, 1997, Entrez Medline query.

Krieg, et al., "Lymphocyte activation by CpG dinucleotide motifs in prokaryotic DNA," Feb. 1996, Trends in Microbioloty, vol. 4 No. 2.

Sato, et al., "Immunostimulatory DNA sequences necessary for effective intradermal gene immunization," Jul. 1996, Science V, Entrez Medline query.

Fournier, et al., "Role for low–Affinity Receptor for IgE (CD23) in Normal and Leukemic B–Cell Proliferation." Sep. 15, 1994, Blood, vol. 4 No. 6.

Segal, et al., "Microbial Products Induce Autoimmune Disease by an IL–12–Dependent Pathway." 1997, The American Association of Immunologists.

Klinman, et al., "Contribution of CpG Motifs to the Immunogenicity of DNA Vaccines." 1997, The Journal of Immunology.

* cited by examiner

SEQUENCE LISTING

```
<160> NUMBER OF SEQ ID NOS:  11

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
tgactgtgaa ggttagagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2
tgactgtgaa cgttagagat ga                                              22

<210> SEQ ID NO 3
<211> LENGTH: 22
<212> TYPE: DNA
<213> ORGANISM: Artificial Sequence
```

-continued

```
<220> FEATURE:
<223> OTHER INFORMATION: Oligonucleotide

<400> SEQUENCE: 3
tgactgtgaa ccttagagat ga                                              22

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide

<400> SEQUENCE: 4
tgactgtgaa gcttagagat ga                                              22

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide

<400> SEQUENCE: 5
tgactgtgtt ccttagagat ga                                              22

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide

<400> SEQUENCE: 6
tcactctctt ccttactctt ct                                              22

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7
tgactgtgga ggtcagagat ga                                              22

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
tgactgtgag ggctagagat ga                                              22

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
tgactgtgtt gcaaagagat ga                                              22
```

```
<210> SEQ ID NO 10
<211> LENGTH: 22
<212> TYPE: DNA
<213> ORGANISM: Artificial Sequence
<220> FEATURE:
<223> OTHER INFORMATION: Oligonucleotide

<400> SEQUENCE: 10
tgactgtgaa tgttagagat ga                                            22

<210> SEQ ID NO 11
<211> LENGTH: 14
<212> TYPE: DNA
<213> ORGANISM: Artificial Sequence
<220> FEATURE:
<223> OTHER INFORMATION: Oligonucleotide

<400> SEQUENCE: 11
aattcaacgt tcgc                                                     14
```

US 6,225,292 B1

INHIBITORS OF DNA IMMUNOSTIMULATORY SEQUENCE ACTIVITY

This application claims the benefit of U.S. Provisional Application No. 60/048,793 filed on Jun. 6, 1997, which is incorporated herein by reference.

BACKGROUND FOR THE INVENTION

1. Field of the Invention

The invention relates to immunostimulatory sequences in DNA. The invention further relates to recombinant expression vectors for use in gene therapy.

2. History of the Related Art

Recombinant expression vectors are the tools which researchers and clinicians use to achieve the goals of gene therapy and gene immunization. In gene therapy, viral and non-viral vectors are used to deliver an expressible gene into a host to replace a missing or defective gene, or to otherwise supply the host with a therapeutically beneficial polypeptide. In gene immunization, mostly non-viral vectors are used to induce an immune response by the host to an expressed antigen.

One of the obstacles to successful clinical practice of both gene therapy and gene immunization has been the often transient nature of the gene expression achieved in vivo. Transient gene expression is less problematic in gene immunization, where immune responses sufficient for certain immunization schemes may be stimulated by even short-term exposure to expressed antigen. In addition, several options are available to boost the host immune response to antigen, including use of the vector itself as an adjuvant for the desired immune response by exposing the host to non-coding, immunostimulatory nucleotide sequences (ISS-ODN) present in the vector (Sato, et al., *Science*, 273:352–354 (1996)).

However, in a gene therapy protocol, premature loss of gene expression deprives the host of the potential benefits of the therapy (Friedmann, *Scientific American*, "Making Gene Therapy Work" (June 1997)). Repetitive dosing to extend exposure of the host to a therapeutic polypeptide can require that different vectors be used to deliver each dose so the host immune response to vector antigens is minimized (Tripathy, et al., *Nature Med.*, 2:545–550 (1996)).

One potential source of vector immunogenicity are ISS-ODN in the genome of the microbial species used to construct recombinant expression vectors. To explain, the CpG motifs which characterize ISS-ODN are present in bacteria and viruses (including retroviruses) at a much greater frequency than is seen in vertebrate genomes. One consequence of ISS-ODN activity is the ISS-ODN induced production of cytokines such as interferon-α (INF-α), INF-γ and interleukin-12 (IL-12). This ISS-ODN induced inflammation is believed to be defensive against microbial infection in vertebrates and is also believed to be produced in response to ISS-ODN introduced into a host as oligonucleotides or as part of a recombinant expression vector.

SUMMARY OF THE INVENTION

The invention provides compounds consisting of oligodeoxynucleotides, ribonucleotides or analogs thereof which specifically inhibit the immunostimulatory activity of ISS-ODN. ISS-ODN induced secretion of INF-α in particular can suppress recombinant gene expression and directly impedes mRNA and protein synthesis in transfected cells. Thus, inhibition of ISS-ODN activity substantially avoids ISS-ODN induced loss of gene expression, thereby prolonging the availability of the expressed polypeptide to a host undergoing gene therapy or gene immunization with an ISS-ODN containing recombinant expression vector. Further, the need for repetitive dosing to prolong availability of expressed proteins and for extensive reengineering of recombinant expression vectors to eliminate ISS-ODN sequences is avoided through use of the compounds of the invention.

The compounds of the invention are also useful in modulating the immunostimulatory activity of ISS-ODN administered as adjuvants to boost host immune responses to antigen in, for example, immunotherapy. In this respect, the compounds of the invention permit exquisite control over the effect of ISS-ODN based adjuvants in a host.

Further, the compounds of the invention reduce host inflammation generated in response to an infection by an ISS-ODN containing bacteria or virus. Advantageously, the compounds of the invention can be administered to inhibit ISS-ODN activity exerted by a microbe even if the identity of the particular ISS-ODN present in the microbe is unknown. Thus, the compounds of the invention can be considered to be broad spectrum anti-inflammatory agents.

In one aspect, the ISS-ODN inhibitory compounds of the invention are synthesized oligonucleotides (I-ON) which are comprised of the following general primary structures:

5'-Purine—Purine-[Y]-[Z]-Pyrmidine-Pyrimidine-3' or

5'-Purine—Purine-[Y]-[Z]-Pyrmidine-pPyrimidine-3' where Y is any naturally occurring or synthetic nucleotide except cytosine and is preferably guanosine or inosine (for RNA I-ON). In general, Z is any naturally occurring or synthetic nucleotide or repeat of the same nucleotide. Preferably, when Y is inosine, Z is inosine or one or more guanosine(s). Where Y is guanosine, Z is preferably guanosine or one or more unmethylated cytosine(s). However, when Y is not guanosine or inosine, Z is guanosine or inosine. Most preferably, the 5' purines are the same nucleotide, as are the 3' pyrimidines. For example, where  is YZ, the 5' purines and 3' pyrimidines may be AATT, AGTT, GATT, GGTT, AATC, AG**TC, and so forth. Any sequences present which flank the hexamer core sequence are constructed to substantially match the flanking sequences present in any known ISS-ODN.

Inhibitory I-ON of the invention are prepared in a pharmaceutically acceptable composition for use in a host. I-ON may be mixed into the composition singly, in multiple copies or in a cocktail of different I-ON. Alternatively, the inhibitory I-ON of the invention may be incorporated into a recombinant expression vector. The inhibitory I-ON can also be provided in the form of a kit, comprising inhibitory I-ON and recombinant expression vector constructs which contain, or are susceptible to insertion of, a gene of interest.

A particular advantage of the I-ON of the invention is that they can be used to target ISS-ODN in any ISS-ODN containing recombinant expression vector or microbe, whether or not the nucleotide composition of the vector or microbe is known. Indeed, it is not necessary that the existence, identity or location of ISS-ODN in the vector or microbe be known. If ISS-ODN are not present in the vector or microbe, the I-ON of the invention will simply have no effect. However, if ISS-ODN are present in the vector or microbe, it can be expected that their immunostimulatory activity will be inhibited in a dose-dependent manner by the I-ON even if the specific structure or location of the ISS-ODN in the vector or microbe is not known.

Thus, in another aspect, the invention provides a simple and effective alternative to the arduous task of eliminating ISS-ODN activity from recombinant expression vectors by identifying all ISS-ODN present in the vector and removing them.

Further in this regard, the invention provides methods for screening recombinant expression vectors for the presence of ISS-ODN and for identifying additional inhibitory I-ON. In the former respect, the presence of ISS-ODN in a recombinant expression vector is confirmed by incubating the vector in a population of lymphocytes with an I-ON of known inhibitory activity and comparing the difference, if any, in the level of ISS-induced cytokine production by the lymphocytes before and after I-ON incubation.

In the latter respect, additional inhibitory I-ON having the characteristics disclosed herein are identified by their ability to inhibit the immunostimulatory activity of a known ISS-containing polynucleotide or recombinant expression vector.

In yet another aspect, the invention further provides a useful anti-inflammatory agent for use in inhibiting the immunostimulatory activity of any ISS-ODN present in an infectious bacterium or virus.

In addition, the invention provides useful means for modulating the immunostimulatory activity of ISS-ODN supplied to a host for immunostimulation (e.g., as an adjuvant).

DETAILED DESCRIPTION OF THE INVENTION

A. Activity and Structure of IIS-ON

1. IIS-ON Activity and Screening Assay

Figure 1:
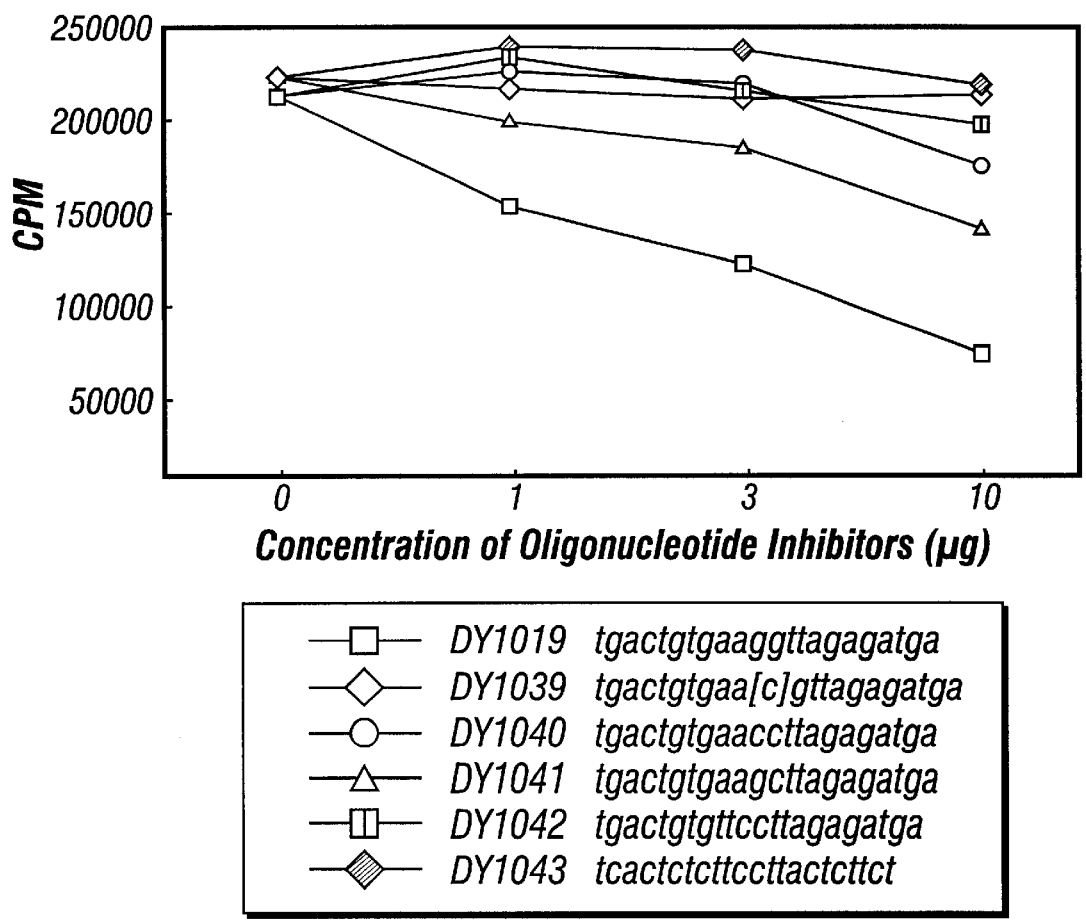
FIG. 1 is a graph which represents in vivo inhibition of ISS-ODN immunostimulatory activity by inhibitory I-ON of the invention (I-ON DY1019 (SEQ ID NO:1) and DY1041 (SEQ ID NO:4) (having hexamer regions consisting of, respectively, AAGGTT and AAGCTT)). Lymphocyte proliferation stimulated in a murine model by the ISS-ODN (DY1038, having a hexamer region consisting of AACGTT) was compared in the presence or absence of the I-ON. A decline in measured counts-per-minute (CPM; vertical axis) represents inhibition of ISS-ODN immunostimulatory activity in the Figure. Dosages for each I-ON tested are shown along the horizontal axis. DY1039 (SEQ ID NO:2) (an ISS-ODN with the cytosine), DY1040 (SEQ ID NO:3), DY1042 (SEQ ID NO:5) and DY1043 (SEQ ID NO:6) (all with CC dinucleotides in place of the CG dinucleotide of DY1038) served as controls. To confirm the location of potential competition with DY1038, all of the oligonucleotides were identical to DY1038 except for the hexamer regions identified and DY1043 (an irrelevant sequence control).

The IIS-ON of the invention reduce the immunostimulatory effect of ISS-ODN. Structurally, ISS-ODN are non-coding oligonucleotides 6 mer or greater in length which may include at least one unmethylated CG motif. The relative position of each CG sequence in ISS-ODN with immunostimulatory activity in certain mammalian species (e.g., rodents) is 5'-CG-3' (i.e., the C is in the 5' position with respect to the G in the 3' position). Many known ISS-ODN flank the CG motif with at least two purine nucleotides (e.g., GA or AA) and at least two pyrimidine nucleotides (e.g., TC or TT) to enhance the B lymphocyte stimulatory activity of the immunostimulatory polynucleotide (see, e.g., Krieg, et al., *Nature*, 374:546–549, 1995).

Functionally, ISS-ODN enhance the cellular and humoral immune responses in a host, particularly lymphocyte proliferation and the release of cytokines (including IFN) by host monocytes and natural killer (NK) cells. Bacterial DNA contains unmethylated CpG dinucleotides at a frequency of about one per every 16 bases. These dinucleotides are also present in certain viral species, but are notably underrepresented in vertebrate species.

It is believed that the ability of mycobacteria as well as other bacterial and viral species to stimulate lymphocyte proliferation, IL-12 production, tumor necrosis factor (TNF) production, natural killer (NK) cell activity and IFN-$\gamma$ secretion is owed to the presence of ISS-ODN in bacterial and viral DNA (see, e.g., Krieg, *Trends in Microbiology*, 4:73–76 (1996)). In contrast, CpG suppression and methylation in vertebrates may be an evolutionary response to the threat of bacterial and viral infection. Interestingly, a CpG containing oligonucleotide comparable to bacterial ISS-ODN has also recently been implicated in the onset and exacerbation of autoimmune disease through an IL-12 dependent pathway (Segal, et al., *J. Immunol.*, 158:5087 (1997)).

Immuostimulation by synthetic ISS-ODN in vivo occurs by contacting host lymphocytes with, for example, ISS-ODN oligonucleotides, ISS-ODN oligonucleotide-conjugates and ISS-containing recombinant expression vectors (data regarding the activity of ISS-ODN conjugates and ISS-ODN vectors are set forth in co-pending, commonly assigned U.S. patent application Ser. Nos. 60/028,118 and 08/593,554; data from which is incorporated herein by reference solely to demonstrate ISS-ODN immunostimulatory activity in vivo). Thus, while native microbial ISS-ODN stimulate the host immune system to respond to infection, synthetic analogs of these ISS-ODN may be useful therapeutically to modulate the host immune response not only to microbial antigens, but also to tumor antigens, allergens and other substances (id.).

Although the invention is not limited by any theory regarding the mechanism of action of the IIS-ON, it is believed that they compete with ISS-ODN for binding to the cellular membrane of host lymphocytes. The region of ISS-ODN which confers their immunostimulatory activity is believed to be the 6 mer or greater length of nucleotides which include an unmethylated dinucleotide (e.g., CpG). Therefore, it is believed that the presence of a region of about 6 mer or greater length having at least one competing dinucleotide (defined as [Y]-[Z] and [Y]-poly[Z] in the formulae set forth below) therein confers ISS-inhibitory activity on the IIS-ON of the invention.

Thus, the inhibitory compounds of the invention are synthesized oligonucleotides (IIS-ON) which inhibit the immunostimulatory activity of ISS-ODN in vertebrates and vertebrate immune cells. To identify IIS-ON from a pool of synthesized candidate IIS-ONs, the following steps provide a simple and efficient means of rapidly screening the candidate pool:

a. A population of cultured, antigen stimulated lymphocytes and/or monocytes is contacted with an ISS-ODN to induce lymphocyte proliferation, IFN$\beta$, IFN-$\alpha$, IFN-$\gamma$, IL-12 and IL-18 cytokine secretion and/or IgG2 antibody production.

b. Any change in the number of lymphocytes, levels of secreted IFN$\beta$, IFN-$\alpha$, IFN-$\gamma$, IL-12 and IL-18 cytokines, IgG1 or IgG2 antibody levels or IgE antibody levels in the cell culture after contact with the ISS-ODN is measured.

c. The cells are contacted with the candidate IIS-ON.

d. Any change in the number of lymphocytes, levels of secreted cytokines, IgG2 antibody levels or IgE antibody levels in the population of cells after contact with the oligonucleotide is measured.

A decline in any of these values (except IgG1 and IgE antibodies) as compared to the measurements taken in step (2) indicates that the candidate oligonucleotide is an IIS-ON of the invention; i.e., it inhibits the immunostimulatory activity of ISS-ODN. Alternatively, a rise in measured levels of IgG1 or IgE antibodies is an indirect indicator of a rise in a Th2-type lymphocyte response, indicating that the Th1 stimulatory activity of ISS-ODN has declined in the presence of the IIS-ODN. Assay techniques suitable for use in performing the steps above are illustrated in the Examples below. In view of the teaching of this disclosure, other assay techniques for measuring changes in ISS-ODN induced lymphocyte proliferation or cytokine secretion will be apparent to those of ordinary skill in the art.

The screening method can also be used to detect ISS-ODN in a sample of immune cells taken from the host. This aspect of the invention is useful in confirming the presence of ISS-ODN containing antigens (e.g., microbial antigens) and autoantigens in the host. To this end, the steps of the above-described screening method are modified to include the steps of:

a. Obtaining a sample of immune cells from the host, which cells are believed to been exposed to an antigen or autoantigen.

b. Measuring the levels of lymphocyte proliferation in; IFN$\beta$, IFN-$\alpha$, IFN-$\gamma$, IL-12 and IL-18 cytokine secretion from; IgG1 and IgG2 antibody production by; or IgE antibody production by, the sample of host immune cells.

c. Contacting the sample of host immune cells with an IIS-ON.

d. Measuring any change in the number of lymphocytes or levels of secreted IFN$\beta$, IFN-$\alpha$, IFN-$\gamma$, IL-12 and IL-18 cytokines and/or levels of IgE or IgG1 antibodies in the sample of host immune cells after contact with the IIS-ON, wherein a decline in any of the measured values for lymphocyte proliferation, cytokine secretion or IgG2 antibody production, as well as an increase in IgG1 and IgE antibody production, as compared to the measurements taken in step (b) indicates that an ISS-ODN subject to inhibition by the IIS-ON is present in the sample of host immune cells.

2. Exemplary IIS-ON Structure

Particular IIS-ON which inhibit the activity of CpG motif-containing ISS-ODN include those oligonucleotides which are comprised of the following general primary structure:

5'-Purine—Purine-[Y]-[Z]-Pyrmidine-Pyrimidine-3' or

5'-Purine—Purine-[Y]-[Z]-Pyrimidine-polyPyrimidine-3' where Y is any naturally occurring or synthetic nucleotide except cytosine and is preferably guanosine, adenosine or inosine (for RNA IIS-ON), most preferably guanosine. In general, Z is any naturally occurring or synthetic nucleotide or repeat of the same nucleotide. Preferably, where Y is inosine, Z is inosine or one or more guanosine(s). Where Y is guanosine, Z is preferably guanosine or one or more unmethylated cytosine(s). Where Y is adenosine, Z is preferably guanosine. However, when Y is not guanosine, adenosine or inosine, Z is guanosine, adenosine or inosine. Most preferably, the 5' purines are the same nucleotide, as are the 3' pyrimidines. For example, where  is YZ, the 5' purines and 3' pyrimidines may be AATT, AGTT, GATT, GGTT, AATC, AG**TC, and so forth.

The core hexamer structure of the foregoing IIS-ON may be flanked upstream and/or downstream by any number or composition of nucleotides or nucleosides. However, IIS-ON will preferably be either 6 mer in length, or between 6 and 45 mer in length, to enhance uptake of the IIS-ON and to minimize non-specific interactions between the IIS-ON and the target recombinant expression vector or host cells. Preferably, any IIS-ON flanking sequences present are constructed to match the flanking sequences present in any known ISS-ODN (such as the flanking sequence DY1038 (TTGACTGTG****AGAGATGA), where **** is the immunostimulatory hexamer sequence. Those of ordinary skill in the art will be familiar with, or can readily identify, reported nucleotide sequences of known ISS-ODN. For ease of reference in this regard, the following sources are especially helpful:

Yamamoto, et al., *Microbiol. Immunol.,* 36:983 (1992)

Ballas, et al., *J. Immunol.,* 157:1840 (1996)

Klinman, et al., *J. Immunol.,* 158:3635 (1997)

Sato, et al., *Science,* 273:352 (1996)

Each of these articles are incorporated herein by reference for the purpose of illustrating the level of knowledge in the art concerning the nucleotide composition of ISS-ODN.

Particular inhibitory IIS-ON of the invention include those having the following hexamer sequences:

1. IIS-ODN having "GG" dinucleotides: AAGGTT, AGGGTT, GGGGTT, GGGGTC, AAGGTC, AAGGCC, AGGGTT, AGGGTC, GAGGTT, GAGGTC, GAGGCC, GGGGCT and so forth.
2. IIS-ODN having "GC" dinucleotides: AAGCTT, AGGCTC, AGGCCC, GAGCTT, GAGCTC, GAGCCC, GGGGCT, GGGCTC, GGGCCC, AAGCCC, AAGCCT, AGGCCT, GAGCCT and so forth.
3. Inosine and/or adenosine subsitutions for nucleotides in the foregoing hexamer sequences made according to the formulae set forth above.

IIS-ON hexamers with especially strong expected inhibitory activity are those with GG and GC competing dinucleotides, particularly AAGGTT (DY1019 in the Figures), AAGCTT (DY1041 in the Figures), AGGGCT, and GAGGTT (including their 3' Pyrimidine-pPyrimidine analogs).

IIS-ON may be single-stranded or double-stranded DNA, single or double-stranded RNA and/or oligonucleosides. The nucleotide bases of the IIS-ON which flank the competing dinucleotides may be the known naturally occurring bases or synthetic non-natural bases (e.g., TCAG or, in RNA, UACGI). Oligonucleosides may be incorporated into the internal region and/or termini of the IIS-ON using conventional techniques for use as attachment points for other compounds (e.g., peptides). The base(s), sugar moiety, phosphate groups and termini of the IIS-ON may also be modified in any manner known to those of ordinary skill in the art to construct an IIS-ON having properties desired in addition to the inhibitory activity of the IIS-ON. For example, sugar moieties may be attached to nucleotide bases of IIS-ON in any steric configuration. In addition, backbone phosphate group modifications (e.g., methylphosphonate, phosphorothioate, phosphoroamidate and phosphorodithioate internucleotide linkages) can confer anti-microbial activity on the IIS-ON, making them particuarly useful in therapeutic applications.

The techniques for making these phosphate group modifications to oligonucleotides are known in the art and do not require detailed explanation. For review of one such useful technique, the an intermediate phosphate triester for the target oligonucleotide product is prepared and oxidized to the naturally occurring phosphate triester with aqueous iodine or with other agents, such as anhydrous amines. The resulting oligonucleotide phosphoramidates can be treated with sulfer to yield phophorothioates. The same general technique (excepting the sulfer treatment step) can be applied to yield methylphosphoamidites from methylphosphonates. For more details concerning phosphate group modification techniques, those of ordinary skill in the art may wish to consult U.S. Pat. Nos. 4,425,732; 4,458,066; 5,218,103 and 5,453,496, as well as *Tetrahedron Lett.* at 21:4149 (1995), 7:5575 (1986), 25:1437 (1984) and *Journal Am. Chem. Soc.,* 93:6657 (1987), the disclosures of which are incorporated herein for the sole purpose of illustrating the standard level of knowledge in the art concerning preparation of these compounds.

A particularly useful phosphate group modification is the conversion to the phosphorothioate or phosphorodithioate forms of the IIS-ON oligonucleotides. In addition to their potentially anti-microbial properties, phosphorothioates and phosphorodithioates are more resistant to degradation in vivo than their unmodified oligonucleotide counterparts, making the IIS-ON of the invention more available to the host.

IIS-ON can be synthesized using techniques and nucleic acid synthesis equipment which are well-known in the art. For reference in this regard, see, e.g., Ausubel, et al., *Current Protocols in Molecular Biology,* Chs. 2 and 4 (Wiley Interscience, 1989); Maniatis, et al., *Molecular Cloning: A Laboratory Manual* (Cold Spring Harbor Lab., New York, 1982); U.S. Pat. No. 4,458,066 and U.S. Pat. No. 4,650,675. These references are incorporated herein by reference for the sole purpose of demonstrating knowledge in the art concerning production of synthetic oligonucleotides.

Alternatively, IIS-ON can be obtained by mutation of isolated microbial ISS-ODN to substitute a competing dinucleotide for the naturally occurring CpG motif. Screening procedures which rely on nucleic acid hybridization make it possible to isolate any polynucleotide sequence from any organism, provided the appropriate probe or antibody is available. Oligonucleotide probes, which correspond to a part of the sequence encoding the protein in question, can be synthesized chemically. This requires that short, oligopeptide stretches of amino acid sequence must be known. The DNA sequence encoding the protein can also be deduced from the genetic code, however, the degeneracy of the code must be taken into account.

For example, a cDNA library believed to contain an ISS-containing polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucelotide of interest. Alternatively, a cDNA library can be screened indirectly for expression of peptides of interest having at least one epitope using antibodies specific for the peptides. Such antibodies can be either polyclonally or monoclonally derived and used to detect expression product indicative of the presence of cDNA of interest.

Once the ISS-containing polynucleotide has been obtained, it can be shortened to the desired length by, for example, enzymatic digestion using conventional techniques. The CpG motif in the ISS-ODN oligonucleotide product is then mutated to substitute a competing dinucleotide for the CpG motif. Techniques for making substitution mutations at particular sites in DNA having a known sequence are well known, for example M13 primer mutagenesis through PCR Because the IIS-ON is non-coding, there is no concern about maintaining an open reading frame in making the substitution mutation. However, for in vivo use, the polynucleotide starting material, ISS-ODN oligonucleotide intermediate or IIS-ON mutation product should be rendered substantially pure (i.e., as free of naturally occurring contaminants and LPS as is possible using available techniques known to and chosen by one of ordinary skill in the art).

The IIS-ON of the invention may be used alone or may be incorporated in cis or in trans into a recombinant expression vector (plasmid, cosmid, virus or retrovirus) which may in turn code for any therapeutically beneficial protein deliverable by a recombinant expression vector. For the sake of convenience, the IIS-ON are preferably administered without incorporation into an expression vector. However, if incorporation into an expression vector is desired, such incorporation may be accomplished using conventional techniques which do not require detailed explanation to one of ordinary skill in the art. For review, however, those of ordinary skill may wish to consult Ausubel, *Current Protocols in Molecular Biology,* supra.

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (*Nucleic Acids Res.,* 9:309, 1981), the method of Maxam, et al., (*Methods in Enzymology,* 65:499, 1980), or other suitable methods which will be known to those skilled in the art. Size separation of cleaved fragments is performed using conventional gel electrophoresis as described, for example, by Maniatis, et al., (*Molecular Cloning,* pp. 133–134, 1982).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

If a recombinant expression vector is utilized as a carrier for the IIS-ON of the invention, plasmids and cosmids are particularly preferred for their lack of pathogenicity. However, plasmids and cosmids are subject to degradation in vivo more quickly than viruses and therefore may not deliver an adequate dosage of IIS-ON to substantially inhibit ISS-ODN immunostimulatory activity exerted by a systemically administered gene therapy vector. Of the viral vector alternatives, adeno-associated viruses would possess the advantage of low pathogenicity. The relatively low capacity of adeno-associated viruses for insertion of foreign genes would pose no problem in this context due to the relatively small size in which IIS-ON of the invention can be synthesized.

Other viral vectors that can be utilized in the invention include adenovirus, adeno-associated virus, herpes virus, vaccinia or an RNA virus such as a retrovirus. Retroviral vectors are preferably derivatives of a murine, avian or human HIV retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, $\Psi 2$, PA317 and PA 12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

By inserting one or more sequences of interest into the viral vector, along with another gene which encodes the ligand for a receptor on a specific target cell, for example, the vector can be rendered target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotides of interest.

Alternatively, a colloidal dispersion system may be used for targeted delivery. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., *Nuc. Acids Symp. Ser.*, 19:189 (1988); Grabarek, et al, *Anal. Biochem.*, 185:131 (1990); Staros, et al., *Anal. Biochem.*, 156:220 (1986) and Boujrad, et al., *Proc. Natl. Acad. Sci. USA*, 90:5728 (1993), the disclosures of which are incorporated herein by reference solely to illustrate the standard level of knowledge in the art concerning conjugation of oligonucleotides to lipids).

Targeted delivery of IIS-ON can also be achieved by conjugation of the IIS-ON to a the surface of viral and non-viral recombinant expression vectors, to an antigen or other ligand, to a monoclonal antibody or to any molecule which has the desired binding specificity. A particular IIS-ODN conjugate of interest is one in which an autoantigen or autoantibody is the IIS-ODN conjugate partner. IIS-ODN autoantigen conjugates are useful in boosting host Th2 type immune responses to the autoantigen (suppressing the Th1 responses induced by the autoantigen itself; see, e.g., Conboy, et al., *J. Exp. Med*, 185:439–451 (1997)), while IIS-ODN autoantibody conjugates are useful in inducing passive immunity in a host suffering from an autoimmune condition. Specific methods for delivery of such conjugates, as well as IIS-ON in general, are described in greater detail infra.

Those of ordinary skill in the art will be familiar with, or can readily determine, sources for autoantigens and autoantibodies useful as IIS-ON conjugates. Examples of such conjugate materials include myelin basic protein (see, e.g., sequence and sourcing information provided in Segal, et al, *J. Immunol.*, 158:5087 (1997); Matsuo, et al., *Am. J. Pathol.*, 150:1253 (1997); and Schluesener, *FEMS Immunol. Med. Microbiol.*, 17:179 (1997)); Sjorgen's syndrome autoantigen (see, e.g., Hanjei, et al., *Science*, 276:604 (1997)); hemochromatosis autoantigen (see, e.g., Ruddy, et al, *Genome Res.*, 7:441 (1997)), La/SSB protein (see, e.g., Castro, et al., *Cell Calcium*, 20:493 (1996)); HsEg5 lupus autoantigen (see, e.g., Whitehead, et al., *Arthritis Rheum.*, 39:1635 (1996)); Ki nuclear lupus autoantigen (see, e.g., Paesen and Nuttal, *Biochem. Biophys. Acta*, 1309:9 (1996)); and antibodies thereto (see, e.g., Menon, et al., *J. Autoimmun.*, 10:43 (1997) and Rahman, et al., *Semin. Arthritis Rheum.*, 26:515 (1996) [human antiphospholipid (anti-DNA) monoclonal antibodies]; and, Kramers, et al., *J. Autoimmun.*, 9:723 (1997) [monoclonal anti-nucleosome lupus autoantibodies]). Each of the cited references is incorporated herein solely to illustrate the level of knowledge and skill in the art concerning the identity, activity and structure of autoantigens and autoantibodies.

Examples of other useful conjugate partners include any immunogenic antigen (including allergens, live and attenuated viral particles and tumor antigens), targeting peptides (such as receptor ligands, antibodies and antibody fragments, hormones and enzymes), non-peptidic antigens (coupled via a peptide linkage, such as lipids, polysaccharides, glycoproteins, gangliosides and the like) and cytokines (including interleukins, interferons, erythorpoietin, tumor necrosis factor and colony stimulating factors). Such conjugate partners can be prepared according to conventional techniques (e.g., peptide synthesis) and many are commercially available.

Those of ordinary skill in the art will also be familiar with, or can readily determine, methods useful in preparing oligonucleotide-peptide conjugates. Conjugation can be accomplished at either termini of the IIS-ON or at a suitably modified base in an internal position (e.g., a cytosine or uracil). For reference, methods for conjugating oligonucleotides to proteins and to oligosaccharide moieties of Ig are known (see, e.g., O'Shannessy, et al., *J. Applied Biochem.*, 7:347 (1985), the disclosure of which is incorporated herein by reference solely to illustrate the standard level of knowledge in the art concerning oligonucleotide conjugation). Another useful reference is Kessler: "Nonradioactive Labeling Methods for Nucleic Acids", in Kricka (ed.), *Nonisotopic DNA Probe Techniques* (Acad. Press, 1992)).

Briefly, examples of known, suitable conjugation methods include: conjugation through 3' attachment via solid support chemistry, (see, e.g., Haralambidis, et al., *Nuc. Acids Res.*, 18:493 (1990) and Haralambidis, et al., *Nuc. Acids Res.*, 18:501 (1990) [solid support synthesis of peptide partner]; Zuckermanm, et al., *Nuc. Acids Res.*, 15:5305 (1987), Corey, et al., *Science*, 238:1401 (1987) and Nelson, et al., *Nuc. Acids Res.*, 17:1781 (1989) [solid support synthesis of oligonucleotide partner]). Amino—amino group linkages may be performed as described in Benoit, et al., *Neuromethods*, 6:43 (1987), while thiol-carboxyl group linkages may be performed as described in Sinah, et al., *Oligonucleotide Analogues: A Practical Approach* (IRL Press, 1991). In these latter methods, the oligonucleotide partner is synthesized on a solid support and a linking group comprising a protected amine, thiol or carboxyl group opposite a phosphoramidite is covalently attached to the 5'-hydroxyl (see, e.g., U.S. Pat. Nos. 4,849,513; 5,015,733; 5,118,800 and 5,118,802).

Linkage of the oligonucleotide partner to a peptide may also be made via incorporation of a linker arm (e.g., amine or carboxyl group) to a modified cytosine or uracil base (see, e.g., Ruth, *4th Annual Congress for Recombinant DNA Research* at 123). Affinity linkages (e.g., biotin-streptavidin) may also be used (se e.g., Roget, et al., *Nuc. Acids Res.*, 17:7643 (1989)).

Methods for linking oligonucleotides to lipids are also known and include synthesis of oligo-phospholipid conjugates (see, e.g., Yanagawa, et al., *Nuc. Acids Symp. Ser.*, 19:189 (1988)), synthesis of oligo-fatty acids conjugates (see, e.g., Grabarek, et al., *Anal. Biochem.*, 185:131 (1990)) and oligo-sterol conjugates (see, e.g., Boujrad, et al., *Proc. Natl. Acad. Sci USA*, 90:5728 (1993)).

Each of the foregoing references is incorporated herein by reference for the sole purpose of illustrating the level of knowledge and skill in the art with respect to oligonucleotide conjugation methods.

If to be delivered without use of a vector or other delivery system, IIS-ON will be prepared in a pharmaceutically acceptable composition. Pharmaceutically acceptable carriers preferred for use with the IIS-ON of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringers dextrose), and the like. Preservatives and other additives may also be present such as, for example, antimicrobials, antioxidants, chelating agents, and inert gases and the like. A composition of IIS-ON may also be lyophilized using means well known in the art, for subsequent reconstitution and use according to the invention.

B. Methods for Administering and Using IIS-ON of the Invention

The IIS-ON of the invention are useful in inhibiting the immunostimulatory activity of ISS, wherever present. Thus, IIS-ON are useful as, for example, anti-inflammatory agents for reducing host immune responses to ISS-ODN in bacteria and viruses. IIS-ON are also useful as agents for suppressing the immunostimulatory activity of any ISS-ODN, known or unknown, present in recombinant expression vectors, especially those used for gene therapy and immunization. In addition, IIS-ODN are useful in inhibiting host autoimmune responses stimulated by microbial ISS-ODN and in boosting Th2 type responses to antigen.

In this context, "inhibition" refers to a reduction in the host immune response as compared to the level of ISS-ODN stimulated host immune response prior to IIS-ODN administration. Because ISS-ODN stimulate secretion of certain cytokines (e.g., IL-12, IL-18 and IFNs) and tend to shift the host cellular immune response to the Th1 repertoire, measurements of cytokine levels, cytokine-stimulated lymphocyte proliferation, IgG2 antibody levels (the production of which is indicative of a Th1 lymphocyte response), IgE levels (the suppression of which is indicative of a Th1 lymphocyte response) and IgG1 antibody levels (the production of which is indicative of a Th2 lymphocyte response) are all suitable values for use in detecting IIS-ODN inhibitory activity. Specific examples and details of methods for determining such values are described further infra.

With respect to shifts in the Th1/Th2 repertoire and consequent changes in cytokine levels, it is helpful to recall that CD4+ lymphocytes generally fall into one of two distinct subsets; i.e., the Th1 and Th2 cells. Th1 cells principally secrete IL-2, IFNγ and TNFβ (the latter two of which mediate macrophage activation and delayed type hypersensitivity) while Th2 cells principally secrete IL-4 (which stimulates production of IgE antibodies), IL-5, IL-6 and IL-10. These CD4+ subsets exert a negative influence on one another; i.e., secretion of Th1 lymphokines inhibits secretion of Th2 lymphokines and vice versa. In addition, it is believed that exposure of Th2 cells to cytotoxic T lymphocytes (CTLs) also suppresses TH2 cell activity.

Factors believed to favor Th1 activation resemble those induced by viral infection and include intracellular pathogens, exposure to IFN-β, IFN-α, IFNγ, IL-12 and IL-18, as well as the presence of APCs and exposure to low doses of antigen. Th1 type immune responses also predominate in autoimmune disease. Factors believed to favor Th2 activation include exposure to IL4 and IL-10, APC activity on the part of B lymphocytes and high doses of antigen. Active Th1 (IFNγ) cells enhance cellular immunity and are therefore of particular value in responding to intracellular infections, while active Th2 cells enhance antibody production and are therefore of value in responding to extracellular infections (albeit at the risk of anaphylactic events associated with IL-4 stimulated induction of IgE antibody production). Thus, the ability to shift host immune responses from the Th1 to the Th2 repertoire and vice versa has substantial clinical significance for enhancing and controlling host immunity against infection and allergy. Further, control over Th1/Th2 mediated cytokine release enables one to control host immune responses to self-antigens (having clinical significance for treatment of autoimmune disease) and to recombinant expression vector antigens (having clinical significance for control of gene expression for gene therapy and gene immunization).

For use in modulating the immunogenicity of a recombinant expression vector, the IIS-ON of the invention will be administered according to any means and route by which the target recombinant expression vector is administered to a host, including in vivo and ex vivo routes. Uptake of IIS-ON by host cells occurs at least as robustly as does uptake of therapy and immunization vectors, if not more so due to the small size of IIS-ON as compared to the total dimensions of plasmid, viral and retroviral nucleic acids.

A particular goal of IIS-ON administration in this context is the inhibition of ISS-ODN stimulated, Th1 mediated cytokine production. Thus, a measurable reduction of such cytokine levels in a treated host constitutes IIS-ON therapeutic activity in this embodiment of the invention. IIS-ON therapeutic activity is also demonstrated in this context by prolongation of gene expression as compared to expression levels obtained in the absence of IIS-ON. Those of ordinary skill in the gene therapy and immunization arts will be very familiar with, or can readily ascertain, clinically acceptable means and routes for administration of therapy and immunization vectors and, by extension, IIS-ON.

For use as anti-inflammatory agents, IIS-ON and IIS-ON conjugates will be administered according to any means and route by which known anti-inflammatories and antibiotics are administered. A particular goal of IIS-ODN administration in this context is the inhibition of ISS-ODN stimulated, Th1 mediated cytokine production. Thus, a measurable reduction of such cytokine levels in a treated host constitutes IIS-ODN therapeutic activity in this embodiment of the invention. Those of ordinary skill in the art of treating infectious disease will be very familiar with, or can readily ascertain, clinically acceptable means and routes for administration of anti-inflammatories and antibiotics and, by extension, IIS-ON and their conjugates.

For use as autoimmune modulators, IIS-ON and IIS-ON autoantigen or autoantibody conjugates will be administered according to any means and route by which known therapies for autoimmune disease are practiced. A particular goal of IIS-ODN administration in this context is the inhibition of ISS-ODN stimulated, Th1 mediated IL-12 production. Thus, a measurable reduction of IL-12 levels in an autoimmune host constitutes IIS-ODN therapeutic activity in this embodiment of the invention. Those of ordinary skill in the art of treating autoimmune disease will be very familiar with, or can readily ascertain, clinically acceptable means and routes for administration of IIS-ON and their conjugates.

For use as modulators of ISS-ODN administered as immunostimulants, the IIS-ON and IIS-ON conjugates of the invention will be administered according to any means and route by which the target ISS-ODN is administered to a host, including in vivo and ex vivo routes. For example, where ISS-ODN are administered as adjuvants in an immunization protocol (see, co-pending and commonly assigned U.S. patent application Ser. Nos. 60/028,118 and 08/593,554), it may be desirable to be able to subsequently reduce or eliminate the ISS-ODN immunostimulatory activity to modify the course of therapy. In this context, therefore, IIS-ON serve as ISS-ODN "off" switches, whereby IIS-ON and IIS-ON conjugate activity is demonstrated by a measured reduction in ISS-ODN stimulated cytokine production, ISS-ODN stimulated lymphocyte production, or a shift away from the Th1 lymphocyte repertoire.

For use as adjuvants for Th2 immune responses to extracellular antigen, the IIS-ON of the invention will be administered according to any means and route by which antigen-based vaccines may be administered to a host. Shifts away from the Th1 lymphocyte repertoire are a measure of efficacy for use of IIS-ON and IIS-ON conjugates as Th2 lymphocyte stimulatory adjuvants in the presence of antigen.

A particular advantage of the IIS-ON of the invention is their capacity to exert an ISS-ODN inhibitory activity even at relatively low dosages. Although the dosage used will vary depending on the clinical goals to be achieved, a suitable dosage range is one which provides up to about 1–200 μg of IIS-ON/ml of carrier in a single dosage. In view of the teaching provided by this disclosure, those of ordinary skill in the clinical arts will be familiar with, or can readily ascertain, suitable parameters for administration of IIS-ON according to the invention.

In this respect, the inhibitory activity of IIS-ON is essentially dose-dependent. Therefore, to increase IIS-ON potency by a magnitude of two, each single dose is doubled in concentration. For use in inhibiting ISS-ODN activity (including activity of ISS-ODN in recombinant expression vectors), it is useful to administer the IIS-ON and target ISS-ODN or vector in equivalent dosages, then increase the dosage of IIS-ON as needed to achieve the desired level of inhibition. For use as an anti-inflammatory agent, it is useful to administer the IIS-ON in a low dosage (e.g., about 1 μg/ml to about 50 μg/ml), then increase the dosage as needed to achieve the desired therapeutic goal. Alternatively, a target dosage of IIS-ON can be considered to be about 1–10 μM in a sample of host blood drawn within the first 24–48 hours after administration of IIS-ON.

To maximize the effectiveness of IIS-ON to inhibit ISS-ODN immunostimulatory activity, the IIS-ON are preferably co-administered with the target ISS-ODN or recombinant expression vector. In addition, IIS-ON may be pre-incubated with the target recombinant expression vector prior to administration to the host to reduce the latter's capacity to present ISS-ODN immunostimulatory activity in the host during treatment in a therapy or immunization regime. For use as an anti-inflammatory, the IIS-ON may be co-administered with, or otherwise taken by a host treated with, other anti-inflammatory pharmaceuticals.

To these ends, IIS-ON are conveniently supplied in single dose vials and/or in kits together with suitable dosages of ISS-ODN, recombinant expression vectors or anti-inflammatory agents. In kits including recombinant expression vectors, the IIS-ON and vectors can be pre-mixed in single dosage vials. Means for administering each dosage to a host (e.g., syringes, transdermal patches, iontophoresis devices and inhalers), if required, are included in each kit.

Examples illustrating the immunoinhibitory activity of IIS-ON are set forth below. The examples are for purposes of reference only and should not be construed to limit the invention, which is to be defined by the appended claims. All abbreviations and terms used in the examples have their expected and ordinary meaning unless otherwise specified.

EXAMPLE I

Assay to Confirm IIS-ON Inhibitory Activity As Measured by a Reduction in Lymphocyte Proliferation Splenocytes from immunologically naive female Balb/c mice (6–8 weeks of age) were harvested from each animal. Supernatants of the harvested splenocytes were incubated with 1 μg/ml of the DY1018 ISS-ODN or 1 μg/ml of the DY1038 ISS-ODN in normal saline (all oligonucleotide sequences are set forth in the legend to the FIGURES and in the Description of Drawings). The backbones of both DY1018 and DY1038 were modified as phosphorothioates. In this context, the ISS-ODN served as nonspecific adjuvants for in vitro stimulation of the immune system.

Within 4 hours of ISS-ODN contact, the supernatants were incubated with various concentrations of IIS-ON or a control. DY1039 (SEQ ID NO:2) (an ISS with the cytosine methylated), DY1040 (SEQ ID NO:3) and DY1043 (SEQ ID NO:6) (the latter with CC dinucleotides in place of the CO dinucleotide of DY1018 and DY1038) served as controls. To confirm the location of potential competition with DY1018 and DY1038, all of the oligonucleotides were identical to DY1038 (FIGS. 1 and 3) or DY1018 (FIG. 2) except for the hexamer regions identified in the FIGURES and DY1043 (an irrelevant sequence control).

Lymphocyte proliferation pre- and post-IIS-ODN administration was measured (as a function of counts per minute) using conventional assay techniques. Any observable changes in lymphocyte proliferation among the supernatants were noted. Values shown in FIGS. 1 through 3 are averages for each group of mice tested.

Figure 2:
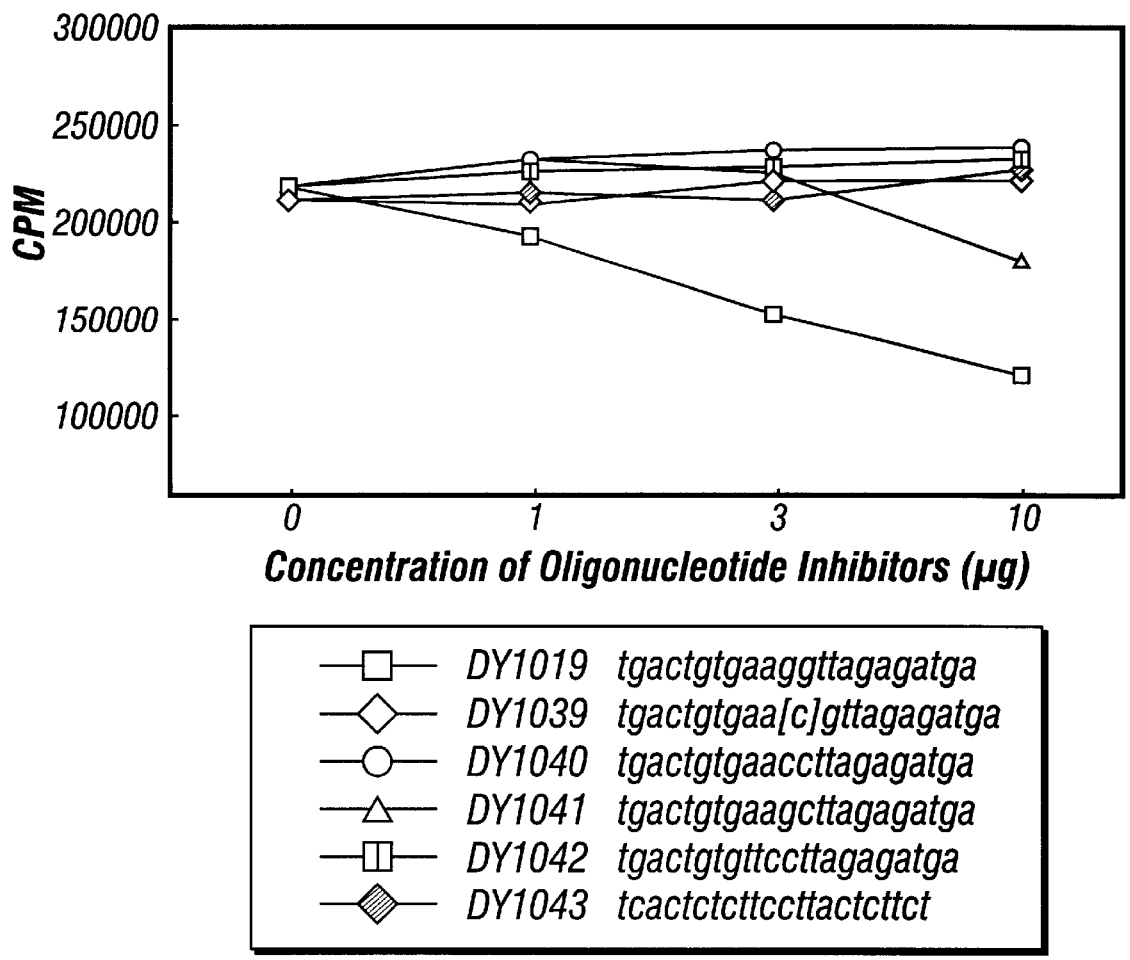
FIG. 2 is a graph which confirms in vivo dose dependent inhibition of ISS-ODN immunostimulatory activity by the DY1019 and DY1041 I-ON of the invention. Lymphocyte proliferation stimulated in a murine model by a different ISS-ODN than the one tested in the experiment of FIG. 1 (DY1018) was compared in the presence or absence of the I-ON. A decline in measured counts-per-minute (CPM; vertical axis) represents inhibition of ISS-ODN immunostimulatory activity in the Figure. Dosages for each I-ON tested are shown along the horizontal axis. Inhibitory activity of I-ON DY1019 and DY-1041 increased with dosage, with the increase in activity of DY1019 being proportional to the increase in dosage. To confirm the location of potential competition with DY1018, DY1019 and DY1041 are identical to DY1018 except for the hexamer regions identified.
Figure 3:
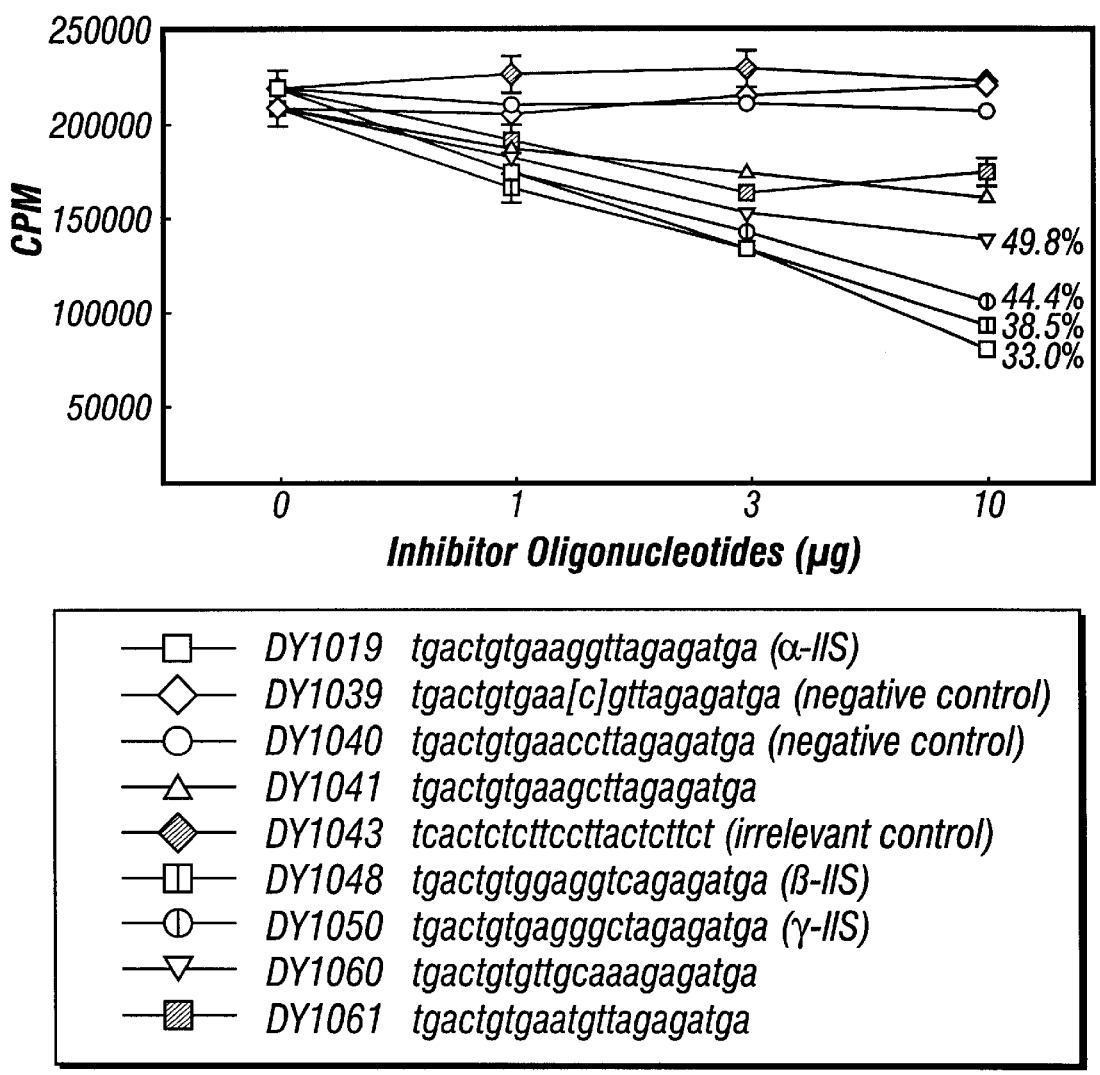
FIG. 3 is a graph which represents in vivo dose dependent inhibition of ISS-ODN immunostimulatory activity by several inhibitory I-ON of the invention. Lymphocyte proliferation stimulated in a murine model by DY1038 was compared in the presence or absence of the I-ON. A decline in measured counts-per-minute (CPM; vertical axis) represents inhibition of ISS-ODN immunostimulatory activity in the Figure. Dosages for each I-ON tested are shown along the horizontal axis. In descending order, the most inhibitory activity was displayed by I-ON DY1019, DY-1041, DY1048 (SEQ ID NO:7), DY1050 (SEQ ID NO:8) and DY1060 (SEQ ID NO:9) (the latter have hexamer regions consisting of, respectively, AGGGTT, GAGGTC and TTGCAA). DY1039 (an ISS-ODN with the cytosine methylated), DY1040 and DY1043 (the latter with CC dinucleotides in place of the CG dinucleotide of DY1038) served as controls. To confirm the location of potential competition with DY1038, all of the oligonucleotides were identical to DY1038 except for the hexamer regions identified and DY1043 (an irrelevant sequence control).

The results of these assays are shown in FIGS. 1 through 3. With respect to both DY1038 (FIGS. 1 and 3) and DY1018 (FIG. 2), the strongest inhibition of ISS immunostimulatory activity by inhibitory IS-ON of the invention in these experiments was demonstrated by IIS-ON DY1019 )SEQ ID NO:1) (having a hexamer region consisting of AAGGTT). Other strongly inhibitory IIS-ON tested were DY1048 (hexamer region=GAGGTC), DY1050 (SEQ ID NO:8) (hexamer region=AGGGCT), DY1060 (SEQ ID NO:9) (hexamer region=TTGCAA) and DY1041 (hexamer region=AAGCTT) (FIG. 3). Inhibitory strength was dose-dependent in a generally proportional relationship of dosage to reduction in lymphocyte proliferation measured.

EXAMPLE II

Assay to Confirm IIS-ON Inhibitory Activity As Measured by a Reduction in INF-γ Secretion Groups of mice were immunized as described in Example I, sacrificed and their splenocytes harvested. Supernatants of harvested splenocytes was incubated with 1 µg/ml of DY1018 ISS-ODN in saline as described in Example I. Within 4 hours, the supernatants were incubated with various concentrations of IIS-ON or a control. DY1039 (an ISS with the cytosine methylated), DY1040 and DY1043 (the latter with CC dinucleotides in place of the CG dinucleotide of DY1018) served as controls (all oligonucleotide sequences are set forth in the legend to the FIGURES and in the Description of Drawings). To confirm the location of potential competition with DY1018, all of the oligonucleotides were identical to DY1018 except for the hexamer regions identified and DY1043 (an irrelevant sequence control).

IFN-γ levels were measured pre- and post- IIS-ODN contact. Any observable changes in IFN-γ secretion (pg/ml supernatants) among the supernatants were noted. Values shown in FIG. 4 are averages for each group of mice tested.

Figure 4:
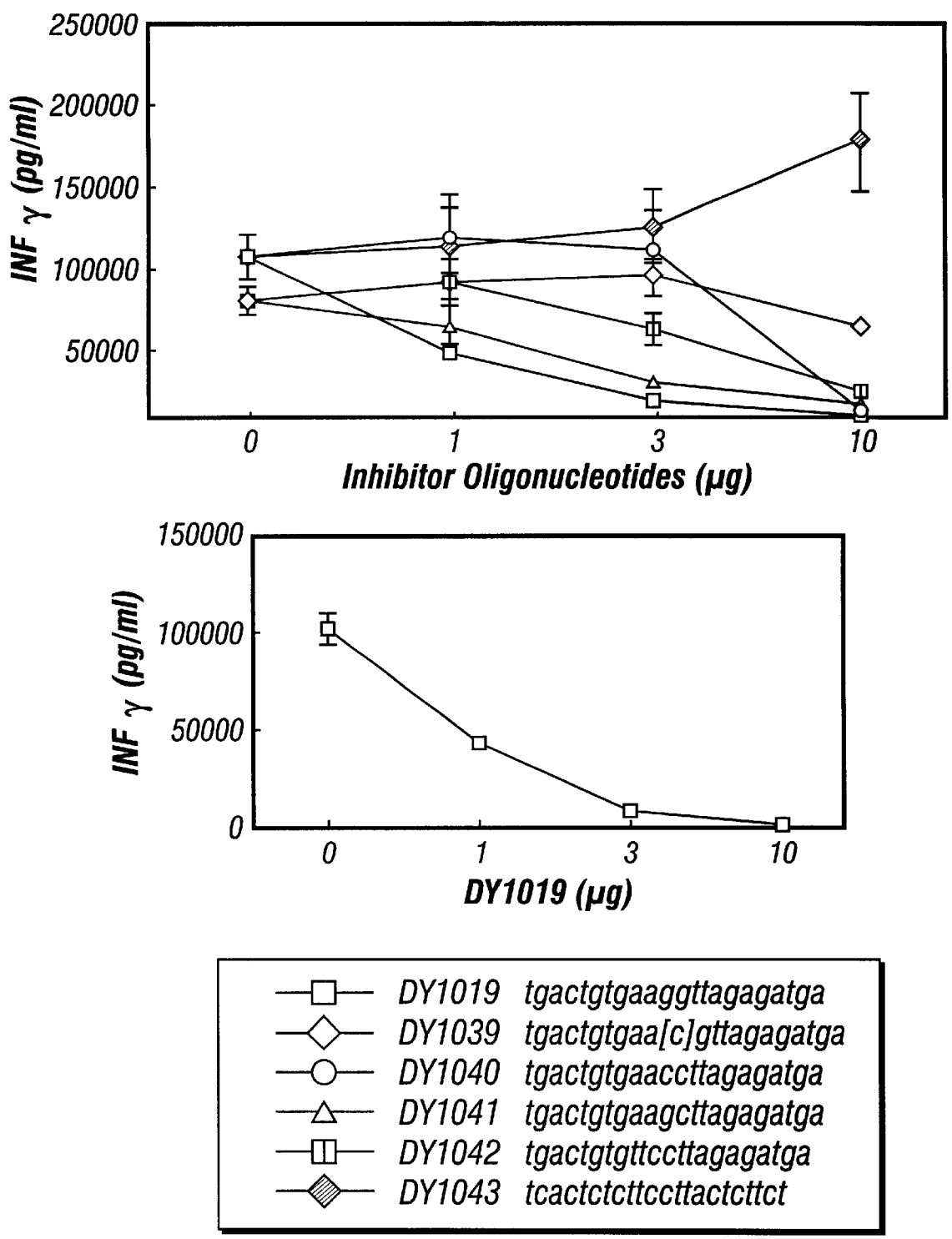
FIG. 4 is a graph which represents in vivo dose dependent inhibition of ISS-ODN immunostimulatory activity by inhibitory I-ON of the invention. INF-$\gamma$ production stimulated by DY1018 ISS-ODN in a murine model was compared in the presence or absence of the I-ON. A decline in measured INF-$\gamma$ (vertical axis) represents inhibition of ISS-ODN immunostimulatory activity in the Figure. Dosages for each I-ON tested are shown along the horizontal axis. Some inhibitory activity was observed for all but one I-ON, with the most activity being displayed by I-ON DY1019 and DY-1041, as well as DY1042 (having a hexamer region consisting of TTCCTT). The insert separates out the data for inhibition of INF-$\gamma$ production by DY1019. To confirm the location of potential competition with DY1018, all of the oligonucleotides were identical to DY1018 except for the hexamer regions identified and DY1043 (an irrelevant sequence control).

The results of these assays are shown in FIG. 4. Again, the strongest inhibition of ISS immunostimulatory activity by inhibitory IIS-ON of the invention in these experiments was demonstrated by IIS-ON DY1019 (having a hexamer region consisting of AAGGTT). DY1041 (hexamer region= AAGCTT) was also strongly inhibitory, even at low dosage (1 µg/ml saline). At a higher dosage (10 µg/ml), INF-γ levels began to decline in control mice as well.

EXAMPLE III

IIS-ODN Boosting of Th2 Type Immune Responses to Antigen

Figure 5:
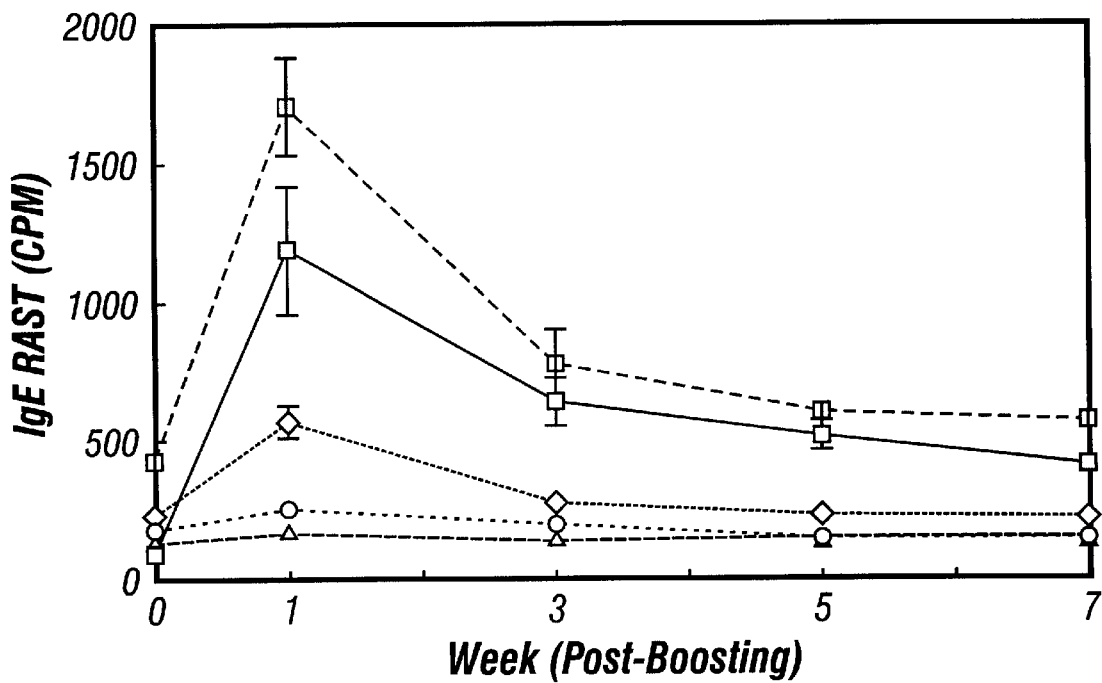
FIG. 5 is a graph which represents the adjuvant properties of IIS-ODN, whereby a Th2-type cellular immune response in antigen ($\beta$-galactosidase) immunized mice is induced by co-administration of the antigen and IIS-ODN DY1019 (identified in the Figure as $\beta$-gal/M-ODN). Th2 responses are represented by IgE levels measured post-boosting. The values obtained are compared to IgE levels measured in mice immunized with antigen and the ISS-ODN composition $\beta$-gal/ISS-ODN (5'-AATTCAACGTTCGC-3), pKISS-3 (a plasmid having three copies of the AACGTT ISS-ODN hexamer in the backbone) and pKISS-0 (a plasmid having no copies of the AACGTT ISS-ODN hexamer in the backbone), as well as mice which received only saline. Potent IgE responses (Th2-type responses) above 1000 CPM were obtained only int he mice which received saline (approximately 1200 CPM at 1 week post-boosting) and P-gal/M-ODN (approximately 1750 CPM at 1 week post-boosting).
Figure 5:
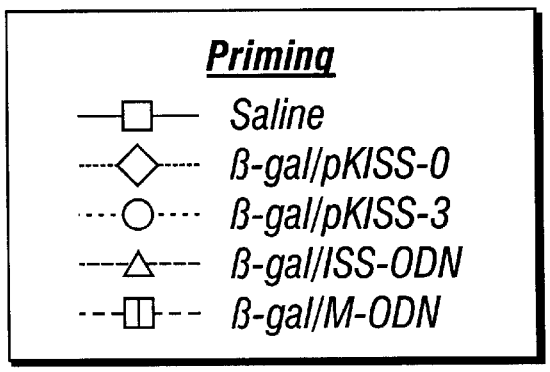

Groups of four Balb/c mice were co-immunized with 10 µg β-galactosidase antigen and 50 µg (in 50 µl normal saline) of IIS-ODN DY1019 (identified in the Figure as β-gal/M-ODN), the ISS-ODN composition β-gal/ISS-ODN (5'-AATTCAACGTTCGC-3'), the β-gal antigen and pKISS-3 (a plasmid having three copies of the AACGTT ISS-ODN hexamer in the backbone), the β-gal antigen and pKISS-0 (a control plasmid having no copies of the AACGTT ISS-ODN hexamer in the backbone), or saline alone. Th2 responses in each group of mice were measured by ELISA as a function of IgE levels obtained post-boosting. As shown in FIG. 5, potent Th2-type responses (above 1000 CPM) were obtained only in the mice which received saline (approximately 1200 CPM at 1 week post-boosting) and β-gal/M-ODN (approximately 1750 CPM at 1 week post-boosting).

Further, high levels of IgG2a antibodies and low levels of IgG1 antibodies (Th1 and Th2 type responses, respectively) were induced in response to antigen in the ISS-ODN treated mice, while the opposite responses were obtained in the IIS-ON treated mice, thus showing a shift toward the Th2 repertoire in the latter group.

The invention having been fully described, modifications of the disclosed embodiments may become apparent to those of ordinary skill in the art. All such modifications are considered to be within the scope of the invention, which is defined by the appended claims.

---

The invention claimed is:

1. A pharmaceutical composition for inhibiting immunostimulation by a immunostimulatory polynucleotide sequence (ISS) comprising a hexamer region consisting of at least one CpG nucleotide motif flanked by two 5' purines and two 3' pyrimidines, the composition comprising:

(a) a nucleic acid molecule comprising a hexameric nucleotide sequence of the formula 5'-Purine—Purine-[Y]-[Z]-Pyrimidine-Pyrimidine-3' or 5'-Purine—Purine-[Y]-[Z]-poly(Pyrimidine)-3';

where Y is any naturally occurring or synthetic nucleotide except cytosine and Z is any naturally occurring or synthetic nucleotide, wherein when Y is not guanosine or inosine, Z is guanosine or inosine; and (b) a pharmaceutically acceptable carrier.

2. The composition according to claim 1 where Y is guanosine or inosine.

3. The composition according to claim 1 where Y is inosine and Z is inosine or guanosine.

4. The composition according to claim 1 where Y is guanosine and Z is guanosine or an unmethylated cytosine.

5. A pharmaceutical composition for inhibiting immunostimulation by an immunostimulatory polynucleotide sequence (ISS) comprising:

(a) a nucleic acid molecule comprising a hexameric nucleotide sequence AAGGTT; and (b) a pharmaceutically acceptable carrier.

6. The composition of claim 5, wherein the nucleic acid molecule is in a sterile vial.

7. The composition of claim 5, wherein the nucleic acid molecule is less than about 45 nucleotides in length.

8. The composition of claim 5, wherein the composition further comprises an antigen.

9. The composition of claim 8 wherein the antigen is conjugated to the nucleic acid molecule.

10. A pharmaceutical composition for inhibiting immunostimulation by an immunostimulatory polynucleotide sequence comprising:

(a) a nucleic acid molecule comprising a hexameric nucleotide sequence AAGCTT; and (b) a pharmaceutically acceptable carrier.

11. The composition of claim 10, wherein the nucleic acid molecule is in a sterile vial.

12. The composition of claim 10, wherein the nucleic acid molecule is less then about 45 nucleotides in length.

13. The composition of claim 10, wherein the composition further comprises an antigen.

14. The composition of claim 13, wherein the antigen is conjugated to the nucleic acid molecule.

15. A pharmaceutical composition for inhibiting immunostimulation by an immunostimulatory polynucleotide sequence comprising:

(a) a nucleic acid molecule comprising a nucleotide sequence AGGGCT; and (b) a pharmaceutically acceptable carrier.

16. The composition of claim 15, wherein the nucleic acid molecule is in a sterile vial.

17. The composition of claim 15, wherein the nucleic acid molecule is less than about 45 nucleotides in length.

18. The composition of claim 15, wherein the composition further comprises an antigen.

19. The composition of claim 18, wherein the antigen is conjugated to the nucleic acid molecule.

20. A pharmaceutical composition for inhibiting immunostimulation by an immunostimulatory polynucelotide sequence comprising:

(a) a nucleic acid molecule comprising a hexameric nucleotide sequence GAGGTT; and (b) a pharmaceutically acceptable carrier.

21. The composition of claim 20, wherein the nucleic acid molecule is in a sterile vial.

22. The composition of claim 20, wherein the nucleic acid molecule is less than about 45 nucleotides in length.

23. The composition of claim 20, wherein the composition further comprises an antigen.

24. The composition of claim 23, wherein the antigen is conjugated to the nucleic acid molecule.

25. A pharmaceutical composition for inhibiting immunostimulation by an immunostimulatory polynucleotide sequence comprising:

(a) a nucleic acid molecule comprising a hexameric nucleotide sequence selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, TTGCAA, AATGTT, GGGGTT, GAGGTC, and AAGCCC; and (b) a pharmaceutically acceptable carrier.

26. The composition of claim 25, wherein the nucleic acid molecule is in a sterile vial.

27. The composition of claim 25, wherein nucleic acid molecule is less than about 45 nucleotides in length.

28. The composition of claim 25, wherein the composition further comprises an antigen.

29. The composition of claim 28, wherein the antigen is conjugated to the nucleic acid molecule.

30. The composition according to any one of claims 1–5, 10, 15, 20 & 25 wherein the nucleic acid molecule is conjugated to a peptide.

31. A kit for use in immunomodulation comprising any one of the nucleic acid molecules according to claims 1–5, 10, 15, 20, 25 & 30 in a sterile vial.

32. The kit according to claim 31 wherein the kit further comprises an antigen.

33. The composition of claim 1, wherein the nucleic acid molecule is in a sterile vial.

34. The composition of claim 1, wherein the nucleic acid molecule is less than about 45 nucleotides in length.

35. The composition of claim 1, wherein the composition further comprises an antigen.

36. The composition of claim 35, wherein the antigen is conjugated to the nucleic acid molecule.

37. A method for reducing the immunostimulatory activity of an immunostimulatory nucleic acid molecule (ISS), comprising:

(a) administering to an individual having an ISS-mediated immune response an effective amount of a nucleic acid molecule comprising a hexameric nucleotide sequence of the formula 5'-Purine—Purine-[Y]-[Z]-Pyrimidine—Pyrimidine-3' or 5'-Purine—Purine-[Y]-[Z]-poly(Pyrimidine)-3', wherein Y is any naturally occurring or synthetic nucleotide except cytosine and Z is any naturally occurring or synthetic nucleotide, wherein when Y is not guanosine or inosine, Z is guanosine or inosine and wherein a reduction in a Th1 type immune response indicates that reduction of immunostimulatory activity has been achieved.

38. The method according to claim 37, wherein the ISS is present in a recombinant expression vector.

39. The method according to claim 38, wherein the recombinant expression vector and the nucleic acid molecule are co-administered to the individual.

40. The method of claim 37, wherein the hexameric nucleotide sequence is selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, AATGTT, GGGGTT, GAGGTC, and AAGCCC.

41. A method for modulating the immunostimulatory activity of an immunostimulatory polynucleotide sequence (ISS) comprising administering to an individual having an ISS-mediated immune response an effective amount of a nucleic acid molecule comprising a nucleotide sequence of the formula 5'-Purine—Purine-[Y]-[Z]-Pyrimidine—Pyrimidine-3' or 5'-Purine—Purine-[Y]-[Z]-poly(Pyrimidine)-3', wherein Y is any naturally occurring or synthetic nucleotide except cytosine and Z is any naturally occurring or synthetic nucleotide, wherein when Y is not guanosine or inosine, Z is guanosine or inosine, and wherein a reduction in a Th1 type immune response or an increase in a Th2 response indicates that modulation of immunostimulatory activity has been achieved.

42. The method according to claim 41, wherein both the ISS and the nucleic acid molecule are administered to a vertebrate host.

43. The method of claim 41, wherein the hexameric nucleotide sequence is selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, AATGTT, GGGGTT, GAGGTC, and AAGCCC.

44. A method for boosting a Th2 type immune response to an antigen in an individual comprising:

administering to an individual an effective amount of a nucleic acid molecule comprising a nucleotide sequence of the formula 5'-Purine—Purine-[Y]-[Z]-Pyrimidine—Pyrimidine-3' or 5'-Purine—Purine-[Y]-[Z]-poly(Pyrimidine)-3', wherein Y is any naturally occurring or synthetic nucleotide except cytosine and Z is any naturally occurring or synthetic nucleotide, wherein when Y is not guanosine or inosine, Z is guanosine or inosine, and wherein a reduction in a Th1 type immune response or an increase in a Th2 response indicates that a boost in a Th2 type immune response to the antigen has been achieved.

45. The method of claim 44, wherein the hexameric nucleotide sequence is selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, AATGTT, GGGGTT, GAGGTC, and AAGCCC.

46. A method for identifying nucleic acid molecules that inhibit the immunostimulatory activity of immunostimulatory oligonucleotides (ISS) comprising:

(a) contacting a population of antigen stimulated immune cells with an ISS, thereby inducing a Th1 response in the cell population;

(b) measuring any change in the Th1 response in the population;

(c) contacting the population of antigen stimulated cells with a candidate nucleic acid molecule; and (d) measuring any change in the Th1 response or a Th2 response, wherein a decrease in the Th1 response and/or an increase in the Th2 response indicates that the nucleic acid molecule inhibits the immunostimulatory activity of the ISS.

47. The method according to claim 46 wherein the candidate inhibitory nucleic acid molecule comprises a hexameric nucleotide sequence of the formula 5' Purine—Purine-[Y]-[Z]-Pyrimidine-3' or 5' Purine—Purine-[Y]-[Z]-Pyrimidine-poly(Pyrimidine)3', where Y is any naturally occurring or synthetic nucleotide except cytosine and Z is any naturally occurring or synthetic nucleotide and wherein when Y is not guanosine or inosine, Z is guanosine or inosine.

48. The method of claims 41, 44, or 46, wherein the Th2 response is measured by measuring IgE production.

49. A pharmaceutical composition comprising:

(a) a nucleic acid molecule identified by the method of claim 46; and (b) a pharmaceutically acceptable carrier.

50. The composition of claim 49, wherein the nucleic acid molecule is in a sterile vial.

51. The composition of claim 49, wherein the nucleic acid molecule is less than about 45 nucleotides in length.

52. The composition of claim 49, wherein the nucleic acid molecule is conjugated to a peptide.

53. The composition of claim 49, wherein the composition further comprises an antigen.

54. The composition of claim 53, wherein the antigen is conjugated to the nucleic acid molecule.

55. A method of reducing Th1-mediated cytokine production, comprising:

administering to an individual an effective amount of a nucleic acid molecule comprising a hexameric nucleotide sequence of the formula 5'-Purine—Purine-[Y]-[Z]-Pyrimidine—Pyrimidine-3' or 5'-Purine—Purine-[Y]-[Z]-poly(Pyrmidine)-3', where Y is any naturally occurring or synthetic nucleotide except cytosine and Z is any naturally occurring or synthetic nucleotide and wherein when Y is not guanosine or inosine, Z is guanosine or inosine, wherein a level of Th1-mediated cytokine is reduced in the individual.

56. The method according to claim 55, wherein the Th1-mediated cytokine production is stimulated by an immunostimulatory polynucleotide sequence.

57. The method of claim 55, wherein the Th1-mediated cytokine is selected from the group consisting of IL-12, interferon-γ, and tumor necrosis factor-β.

58. The method of claim 55, wherein the hexameric nucleotide sequence is selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, AATGTT, GGGGTT, GAGGTC, and AAGCCC.

59. A pharmaceutical composition for inhibiting stimulation of a Th1 immune response, comprising:

(a) a nucleic acid molecule comprising a hexameric nucleotide sequence selected from the group consisting of AAGGTT, AAGCTT, AGGGCT, TTGCAA, and GAGGTC; and (b) a pharmaceutically acceptable carrier.

60. A method for reducing the immunostimulatory activity of an immunostimulatory polynucleotide sequence (ISS), comprising:

administering to an individual having an ISS-mediated immune response an effective amount of a composition according to claim 59, wherein a Th1 type immune response is reduced and the composition is effective in reducing the immunostimulatory activity of an ISS.

61. The method of claims 37, 41, 44, 46 or 60, wherein the Th1 response is measured by measuring a parameter selected from the group consisting lymphocyte proliferation, IFNβ secretion, IFN-α secretion, IFN-γ secretion, IL-12 secretion, and IL-18 secretion.

62. A method for boosting a Th2 type immune response to an antigen in an individual comprising:

administering to an individual an effective amount of a composition according to claim 59, wherein a reduction in Th1 type immune response or an increase in a Th2 response indicates that the composition is effective in boosting Th2 type immune response to the antigen.

63. A method of reducing Th1-mediated cytokine production, comprising:

administering to an individual an effective amount of a composition according to claim 59, wherein a a level of a Th1-mediated cytokine is reduced in the individual.

64. A method of reducing lymphocyte proliferation, comprising:

administering to an individual an effective amount of a composition according to claim 59, wherein lymphocyte proliferation in response to an immunostimulatory sequence is reduced in the individual.

65. The composition of claim 59, wherein the composition further comprises an antigen.

66. The composition of claim 64, wherein the antigen is conjugated to the nucleic acid molecule.

67. The composition of claim 59, wherein the nucleic acid molecule is in a sterile vial.

68. The composition of claim 59, wherein the nucleic acid molecule is less than about 45 nucleotides in length.

69. The composition of claim 59, wherein the nucleic acid molecule is conjugated to a peptide.

70. A pharmaceutical composition for inhibiting stimulation of a Th1 immune response, comprising:

(a) a nucleic acid molecule comprising a hexameric nucleotide sequence of the formula 5'-Purine—Purine-[Y]-[Z]-Pyrimidine—Pyrimidine-3' or 5'-Purine—Purine-[Y]-[Z]-poly(Pyrimidine)-3';

where Y is any naturally occurring or synthetic nucleotide except cytosine and Z is any naturally occurring or synthetic nucleotide, wherein when Y is not guanosine or inosine, Z is guanosine or inosine;

(b) a pharmaceutically acceptable carrier.

71. The composition of claim 70, wherein the nucleic acid molecule is in a sterile vial.

72. The composition of claim 70, wherein the nucleic acid molecule is less than about 45 nucleotides in length.

73. The composition of claim 70, wherein the composition further comprises an antigen.

74. The composition of claim 73, wherein the antigen is conjugated to the nucleic acid molecule.

75. The composition of claim 70, wherein the nucleic acid molecule is conjugated to a peptide.

76. A method for reducing the immunostimulatory activity of an immunostimulatory polynucleotide sequence (ISS), comprising:

administering to an individual having an ISS-mediated immune response an immunoinhibitory amount of a composition according to claim 70, wherein a Th1 type immune response is reduced and the composition is effective in reducing the immunostimulatory activity of an ISS.

77. A method for boosting a Th2 type immune response to an antigen in an individual comprising:

administering to an individual an effective amount of a composition according to claim 70, wherein a reduction in a Th1 type immune response or an increase in a Th2 response indicates that the composition is effective in boosting a Th2 type immune response to the antigen.

78. A method of reducing Th1-mediated cytokine production, comprising:

administering to an individual an effective amount of a composition according to claim 70, wherein a level or a Th1-mediated cytokine is reduced in the individual.

79. A method of reducing lymphocyte proliferation, comprising:

administering to an individual an effective amount of a composition according to claim 70, wherein a reduction in lymphocyte proliferation in response to an immunostimulatory sequence is reduced.

80. A method of reducing lymphocyte proliferation, comprising:

administering to an individual an effective amount of a nucleic acid molecule comprising a hexameric nucleotide sequence of the formula 5'-Purine—Purine-[Y]-[Z]-Pyrimidine—Pyrimidine-3' or 5'-Purine—Purine-[Y]-[Z]-poly(Pyrimidine)-3', where Y is any naturally occurring or synthetic nucleotide except cytosine and Z is any naturally occurring or synthetic nucleotide and wherein when Y is not guanosine or inosine, Z is guanosine or inosine, wherein lymphocyte proliferation in the individual is reduced.

81. The method of claim 80, wherein the lymphocyte proliferation is in response to an immunostimulatory sequence.

82. The method of claim 80, wherein the hexameric nucleotide sequence is selected from the group consisting of AAGGTT, AGGGCT, GAGGTT, AAGCTT, AGGCTC, GAGCTT, GGGCTT, AAGCTC, AGGCTC, GAGCTC, GGGCTC, AAGCCC, AGGCCC, GAGCCC, GGGCCC, AGGCCT, GAGCCT, GGGGCT, AATGTT, GGGGTT, GAGGTC, and AAGCCC.

* * * * *

UNITED STATES PATENT AND TRADEMARK OFFICE
CERTIFICATE OF CORRECTION

PATENT NO. : 6,225,292 B1
DATED : May 1, 2001
INVENTOR(S) : Eyal Raz et al.

It is certified that error appears in the above-identified patent and that said Letters Patent is hereby corrected as shown below:

Claim 12,
"then" should read -- than --;

Claim 66,
Should read -- The composition of claim 65 -- not "64"; and

Claim 70,
Section (a) on the last line after "inosine;" it should read -- inosine; and --

Signed and Sealed this

Nineteenth Day of February, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,225,292 B1
DATED : May 1, 2001
INVENTOR(S) : Raz, Eyal et al.

It is certified that error appears in the above-identified patent and that said Letters Patent is hereby corrected as shown below:

Column 1,
Line 7, following the first paragraph of the specification please insert a second paragraph which reads:

-- This invention was made with Government support under Grant No. AI37305 awarded by the National Institutes of Health. The Government has certain rights in this invention --

Signed and Sealed this

Eighth Day of October, 2002

Attest:

JAMES E. ROGAN
Attesting Officer  Director of the United States Patent and Trademark Office